(12) United States Patent
Steingräber et al.

(10) Patent No.: US 12,409,314 B2
(45) Date of Patent: Sep. 9, 2025

(54) PUMP SYSTEM, CONTROL UNIT AND METHOD FOR OPERATING A PUMP SYSTEM

(71) Applicant: Berlin Heart GmbH, Berlin (DE)

(72) Inventors: Robert Steingräber, Berlin (DE); Matthias Kiesner, Rangsdorf (DE); Alexander Reiprich, Lychen (DE); John C. Woodard, Turramurra (AU)

(73) Assignee: Berlin Heart GmbH, Berlin (DE)

( * ) Notice: Subject to any disclaimer, the term of this patent is extended or adjusted under 35 U.S.C. 154(b) by 531 days.

(21) Appl. No.: 17/775,835

(22) PCT Filed: Nov. 11, 2020

(86) PCT No.: PCT/EP2020/081735
§ 371 (c)(1),
(2) Date: May 10, 2022

(87) PCT Pub. No.: WO2021/094359
PCT Pub. Date: May 20, 2021

(65) Prior Publication Data
US 2022/0387780 A1    Dec. 8, 2022

(30) Foreign Application Priority Data
Nov. 11, 2019  (EP) ..................... 19208405

(51) Int. Cl.
*A61M 60/546* (2021.01)
*A61M 60/122* (2021.01)
(Continued)

(52) U.S. Cl.
CPC ........ *A61M 60/546* (2021.01); *A61M 60/122* (2021.01); *A61M 60/268* (2021.01);
(Continued)

(58) Field of Classification Search
CPC .... A61M 2205/3331; A61M 2230/005; A61M 2230/04; A61M 2230/63; A61M 60/117;
(Continued)

(56) References Cited

U.S. PATENT DOCUMENTS 3,457,909 A    7/1969   Laird
7,572,217 B1   8/2009   Koenig et al.

FOREIGN PATENT DOCUMENTS

DE    26 58 104 A1    12/1977

OTHER PUBLICATIONS

Kitamura T et al., Indirect Measurement Technique for a Portable Artificial Heart Drive System, dated Jan. 1, 1986, pp. 7-11, vol. 25, Nr. 4, ISA Transactions, Instrument Society of America. Pittsburgh, US.

(Continued)

*Primary Examiner* — Amanda K Hulbert
(74) *Attorney, Agent, or Firm* — Crowell & Moring LLP

(57) ABSTRACT

A pump system is provided comprising a diaphragm fluid pump which can be fluidically connected to a heart and/or at least one blood vessel by means of an inlet cannula and an outlet cannula and is adapted for generating a pulsatile fluid flow for supporting a cardiac activity of the heart, a working pressure source connected to the diaphragm fluid pump by means of a pressure line and adapted for providing a working pressure for driving the diaphragm fluid pump, a control unit adapted for controlling the working pressure, a first flow sensor adapted for detecting a first cannula flow signal corresponding to an inlet flow in the inlet cannula or an outlet flow in the outlet cannula, a working pressure sensor adapted for detecting a working pressure signal corresponding to the working pressure in the pressure line.

21 Claims, 12 Drawing Sheets

(51) Int. Cl.
*A61M 60/268* (2021.01)
*A61M 60/427* (2021.01)
*A61M 60/515* (2021.01)
*A61M 60/562* (2021.01)
*A61M 60/585* (2021.01)

(52) U.S. Cl.
CPC ........ *A61M 60/427* (2021.01); *A61M 60/515* (2021.01); *A61M 60/562* (2021.01); *A61M 60/585* (2021.01); *A61M 2205/3331* (2013.01); *A61M 2230/04* (2013.01); *A61M 2230/63* (2013.01)

(58) Field of Classification Search
CPC .............. A61M 60/122; A61M 60/152; A61M 60/178; A61M 60/268; A61M 60/35; A61M 60/427; A61M 60/43; A61M 60/515; A61M 60/523; A61M 60/531; A61M 60/538; A61M 60/546; A61M 60/562; A61M 60/585; A61M 60/869
See application file for complete search history.

(56) References Cited

OTHER PUBLICATIONS

International Search Report with English Translation, dated Feb. 8, 2021, pp. 1-8, issued in International Application No. PCT/EP2020/081735, European Patent Office, Rijswijk, The Netherlands.

PUMP SYSTEM, CONTROL UNIT AND METHOD FOR OPERATING A PUMP SYSTEM

CROSS-REFERENCE TO RELATED APPLICATIONS

This application is a 371 nationalization of international patent application PCT/EP2020/081735 filed Nov. 11, 2022, which claims priority under 35 USC § 119 to European patent application 19208405.1 filed Nov. 11, 2019. The entire contents of each of the above-identified applications are hereby incorporated by reference.

DETAILED DESCRIPTION

Figure 1:
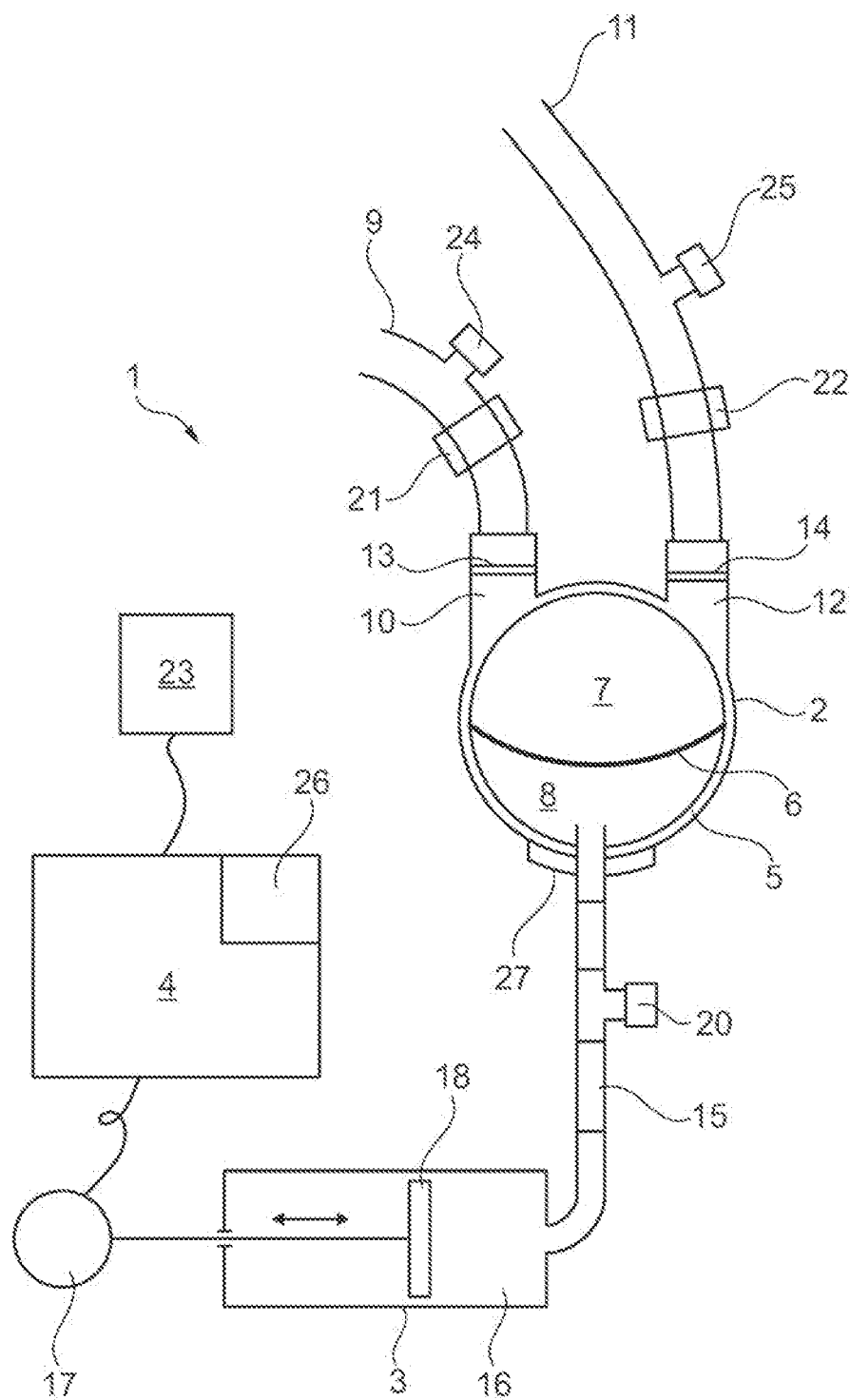
FIG. 1 is a schematic representation of a pump system.

The present application relates to a pump system, comprising a diaphragm fluid pump adapted for generating a pulsatile fluid flow for supporting a cardiac activity, a control unit (also known as a "controller") for such a pump system, and a method for operating such a pump system.

Pump systems for supporting the heart, that is, for supporting a heart activity, are known from the prior art and are also referred to below as a VAD (ventricular assist device). Different types of blood pumps can be used to pump blood in such pump systems, such as diaphragm fluid pumps or rotary fluid pumps. Diaphragm fluid pumps are characterized in that said pumps can generate a pulsatile fluid flow, similar to natural heart activity.

When using a VAD, physiological events or changes in the patient can in many cases only be detected insufficiently, thus also making it difficult to react appropriately to such events or changes, for example, by readjusting operating parameters of the diaphragm fluid pump.

For example, in patients whose cardiac activity improves during treatment with a VAD, weaning should be achieved by gradually reducing the contribution of the VAD to the total blood flow in the circulation of the patient, which can only be achieved by measuring and evaluating changing hemodynamic parameters. This is often not possible or involves invasive diagnostic procedures.

As a further example, patients with Fontan circulation can experience a deterioration in cardiac activity up to and including heart failure (failing Fontan), in the treatment of which by means of VAD it is of great importance to counteract pressure changes in the vena cava in order, on the one hand, to avoid excessive pressures and their negative consequences (for example, damage to the liver or other organs), while on the other hand, to avoid collapsing of the vena cava caused by negative pressure. There is a lack of suitable pump systems for this purpose.

In some acute conditions of the heart muscle, such as a heart attack, strong unloading helps reduce long-term damage. The scar size remains small due to the unloading. However, there are also patients who should be weaned from the system at the end of therapy using cardiovascular support. The heart muscle should be loaded again with these patients. At the same time, the support system should still ensure a minimum blood flow.

In general, there is a lack of pump systems that can be controlled according to actual conditions, in particular instantaneous and/or long-term values of hemodynamic parameters, for providing a blood flow that meets the patient's needs, but at the same time take into account physiological boundary conditions that ensure the safety and health of the patient (these boundary conditions can, for example, comprise ensuring regular opening of the aortic or pulmonary valve or avoiding suction of the heart wall or collapse of the vena cava).

Accordingly, one object of the present application is to accordingly propose a pump system which avoids or reduces said disadvantages. Furthermore, a control unit for such a pump system and a method for operating such a pump system are to be proposed.

The proposed pump system comprises
a diaphragm fluid pump which can be fluidically connected to a heart and/or at least one blood vessel by means of an inlet cannula and an outlet cannula and is adapted for generating a pulsatile fluid flow for supporting a cardiac activity of the heart,
a working pressure source connected to the diaphragm fluid pump by means of a pressure line and adapted for providing a working pressure for driving the diaphragm fluid pump,
a control unit adapted for controlling the working pressure,
a first flow sensor adapted for detecting a first cannula flow signal corresponding to an inlet flow in the inlet cannula or an outlet flow in the outlet cannula,
a working pressure sensor adapted for detecting a working pressure signal corresponding to the working pressure in the pressure line,
the pulsatile fluid flow comprising a plurality of consecutive pumping cycles, the cardiac activity comprising a plurality of consecutive cardiac cycles, and each of the pumping cycles comprising a filling phase and an emptying phase.

A device is referred to here as a diaphragm fluid pump, in the interior of which a cavity is formed, the cavity being divided by a deflectable diaphragm into a pump fluid chamber and a working fluid chamber.

The pump fluid chamber has a fluid inlet that can be connected or is connected to the inlet cannula and a fluid outlet that can be connected or is connected to the outlet cannula. Moving the diaphragm, in particular by deflecting the diaphragm in opposite directions, can vary the size of the pump fluid chamber and can thus generate a negative or positive pressure, through which pump fluid chamber a fluid, in particular blood, can flow into or out of the pump fluid chamber.

The diaphragm fluid pump and/or the inlet and/or outlet cannula can comprise valves which can be arranged, for example, at the fluid inlet and/or at the fluid outlet and can be controlled such that the fluid can flow in through the inlet and out through the outlet during operation. The valves can also be one-way valves, so that even without an active control, the fluid can only flow in through the inlet and/or can only flow out through the outlet.

Repeatedly deflecting the diaphragm to sequentially increase and decrease the pumping fluid chamber creates the pulsatile fluid flow, each pumping cycle comprising the filling phase (also called fill phase) defined by the inflow of fluid into the pump fluid chamber and the emptying phase defined by the outflow of fluid from the pump fluid chamber (not necessarily in that order). Pauses in the diaphragm movement can be provided between the successive filling and emptying phases.

The working fluid chamber can be filled with a working fluid and is connected to the working pressure source by means of the pressure line such that the working pressure source can generate an overpressure and/or a negative pressure in the working fluid chamber for deflecting the diaphragm.

The working pressure source can be, for example, a piston pump comprising a working piston that can be moved in a working chamber, another type of pump or a pneumatic circuit comprising a compressor, an overpressure tank and a vacuum tank. The working fluid can preferably be air, but also another gas or a liquid.

The working pressure signal detected by means of the working pressure sensor can be used by the control unit as a monitoring and/or feedback signal for controlling the working pressure and thus for controlling the pulsatile fluid flow.

All of the pressures mentioned above and below within the pump system can in particular be relative pressures, that is, in particular pressures measured relative to the ambient pressure or also pressures measured relative to a thoracic pressure.

The diaphragm fluid pump and/or the inlet cannula and/or the outlet cannula can be at least partially implantable for using the pump system for supporting the heart. Furthermore, the inlet cannula can be connected, for example, to a ventricle and/or an atrium and/or a vena cava and/or a pulmonary vein, and the outlet cannula can be connected to an aorta and/or a pulmonary artery.

The first flow sensor can be arranged in or on the inlet cannula or the outlet cannula or the fluid inlet or the fluid outlet for detecting the first cannula flow signal. The first flow sensor can be, for example, an ultrasonic flow sensor, a Hall effect sensor, or another type of flow sensor.

Each cardiac cycle typically has a filling phase (diastole, characterized by relaxation of the heart muscle) and an emptying phase (systole, characterized by contraction of the heart muscle) (not necessarily in that order). Cardiac activity is characterized by a number of important parameters, some of which are discussed below.

The duration of a cardiac cycle is referred to as the period of cardiac activity, the reciprocal of which is the pump rate. Preload is understood as the force that counteracts the filling of the ventricles at the end of diastole. Preload is often approximated by end-diastolic pressure, that is, the pressure difference across the filled ventricle (relative to ambient pressure or, preferably, thoracic pressure), or end-diastolic volume, that is, the ventricular filling volume at the end of diastole. The afterload is the force opposing the contraction of the heart muscle during systole and can be estimated from the arterial resistance or the arterial blood pressure. Contractility is the ability of the heart muscle to exert force or build up pressure by contracting.

It is provided that the control unit is further adapted
to determine a time offset between a first point in time that occurs during a first pumping cycle and a second point in time that occurs during a first cardiac cycle,
to determine a hemodynamic parameter set, comprising one or more hemodynamic parameters, based on the time offset and/or the first cannula flow signal and/or the working pressure signal, and
based on a control specification as a specification for the hemodynamic parameter set and/or for the time offset, to determine a time specification as a specification for a beginning and/or a duration of the filling phase and/or the emptying phase of the first pumping cycle and/or at least one second pumping cycle that occurs temporally after the first pumping cycle such that the control specification is achieved.

The first point in time can be defined based on features, in particular repeatedly and/or periodically occurring features of a time profile of a measured variable and/or a pump parameter, for example, a pressure signal and/or a flow signal, in particular the working pressure signal and/or the first cannula flow signal. The second point in time can be defined on the basis of features, in particular features that occur repeatedly and/or periodically depending on the time offset of a time profile of a measured variable and/or a hemodynamic parameter, for example, a pressure signal and/or a flow signal, for example, a cannula pressure signal and/or the first cannula flow signal, or for example, an ECG signal.

The first point in time can be, for example, a beginning or an end of the filling phase or the emptying phase of the first pumping cycle or another point in time during the first pumping cycle. Correspondingly, the second point in time can be, for example, a beginning or an end of the filling phase or the emptying phase of the first pumping cycle or another point in time during the first cardiac cycle.

The time offset can be defined on the basis of features, in particular repeatedly and/or periodically occurring features and/or features of a time profile of a measured variable and/or a pump parameter and/or a hemodynamic parameter that change depending on the time offset, for example, a pressure signal and/or a flow signal, in particular the working pressure signal and/or the first cannula flow signal. The time offset in this case can also be implicitly defined and/or implicitly determinable, that is, be determinable without explicitly determining the first and second points in time.

The control unit can be adapted, for example, to determine the time offset based on a sensor signal or a plurality of sensor signals. For example, the control unit can be adapted to determine the time offset based on the first cannula flow signal as a sensor signal. This is made possible by the fact that the first cannula flow signal is a total flow signal, which therefore contains not only information about the contribution of the diaphragm fluid pump to the total flow, but also information about the contribution of the heart activity to the total flow. Alternatively or additionally, the control unit can be adapted to determine the time offset based on one or more further sensor signals, for example, the working pressure signal and/or an electrocardiographic signal (ECG signal) and/or a cannula pressure signal.

The at least one second pumping cycle can be a pumping cycle (or a plurality of such pumping cycles) immediately following the first pumping cycle, or a pumping cycle (or a plurality of such pumping cycles) occurring only one or more pumping cycles later, for example, also a pumping cycle (or a plurality of such pumping cycles) occurring only considerably later (for example, minutes or hours later).

The time offset represents an important characteristic of the operation of the pump system, the determination of which is fundamental for recognizing physiological events or changes in the patient, which, as changes in the time offset and/or further variables that can be determined based on the time offset, for example, the hemodynamic parameters of the hemodynamic parameter set, are detectable.

This enables an appropriate reaction to such events or changes, in particular by readjusting operating parameters of the diaphragm fluid pump, in particular the time specification. Depending on the choice of the second pumping cycle, the time specification can enable rapid/immediately effective readjustment or gradual/longer-term readjustment (which can then in turn be corrected on the basis of the continuous detection of the time offset). For this purpose, the control unit can also be adapted to determine other time specifications, which relate to further pumping cycles, in addition to the stated time specification, which relates to the first and/or second pumping cycle.

The determination of the time offset and the determination of the hemodynamic parameter set based thereon and the time specification is based on the knowledge that the time offset reflects the property of the diaphragm fluid pump as an additional reservoir in the circuit that can be filled and emptied in principle independently of the heart activity and the filling and emptying phases of which, which can be controlled in relation to cardiac activity, bring numerous advantages. In particular, knowledge and/or variation of the time offset can be used for measuring and/or controlling important variables. These possibilities do not exist, for example, in the case of a rotary fluid pump operated in a pulsatile manner by varying the rotational speed due to the lack of an additional reservoir.

Since the diaphragm fluid pump itself is thus used as a measuring device, the hemodynamic parameter set can be determined non-invasively during operation of the pump system and the time specification can be determined accordingly.

Working together, the determination of the time offset, the determination of the hemodynamic parameter set based thereon and the determination of the time specification thus have the advantage that the pump system can be controlled according to the actual, present conditions, in particular instantaneous or long-term values of hemodynamic parameters, for providing a blood flow that meets the patient's needs and at the same time physiological boundary conditions that ensure the safety and health of the patient can be taken into account by the control specification and/or the time specification.

The control specification can comprise a specific value or value range of one or more hemodynamic parameters of the hemodynamic parameter set and/or the time offset, but can also comprise other types of specifications, for example, a mere direction specification, such as an increase, decrease or maintenance of one or more hemodynamic parameters of the hemodynamic parameter set and/or the time offset.

Determining the hemodynamic parameter set or determining one or more hemodynamic parameters can also mean determining approximate values and/or variables that behave similarly to the respective hemodynamic parameter(s), at least in certain value ranges (such as in the above example of the approximation of the preload due to end-diastolic volume, etc.). In this case, for example, an at least approximately proportionality or another functional relationship that can be reversed at least in some regions can behave in a similar manner.

Determining the time specification such that the control specification is achieved does not necessarily mean that the control specification will actually be achieved in operation. Determining the time specification in this way can also mean that the time specification is determined such that the control specification is likely to be achieved under one or more assumptions, for example, one or more of the following assumptions: an assumption that the time specification is implemented by the control unit; an assumption that the hemodynamic parameters will not change such that the control specification can no longer be achieved; an assumption that the control specification does not result in adjustment of manipulated variables outside respective manipulated variable limits; an assumption that the hemodynamic parameters change such that the control specification can be achieved by means of a time specification that lies within a lower and an upper limit.

The control unit can be adapted to control the working pressure based on the time specification such that the control specification is achieved.

This enables automatic control of the pump system, achieved in particular by feedback of the hemodynamic parameter set and/or the time offset, that is, automatic reaction to physiological events or changes, which has the advantage of not requiring any intervention from the user or medical personnel, at least in certain situations.

Controlling the working pressure such that the control specification is achieved does not necessarily mean that the control specification is actually achieved during operation. Rather, controlling the working pressure in this way means that the working pressure is controlled such that the control specification is likely to be achieved, assuming that the hemodynamic parameters do not change such that the control specification can no longer be achieved.

The pump system can further have a display unit, the display unit being adapted for displaying a proposed setting change determined based on the time specification and/or for displaying at least one hemodynamic parameter of the hemodynamic parameter set.

Alternatively or additionally to the automatic control of the pump system, the information required for manual control or manual intervention can be made possible in this way, which has the advantage that an assessment and evaluation of the situation, for example, by medical staff, is made possible as the basis for the control.

The control unit can be adapted to display one or more hemodynamic parameters of the hemodynamic parameter set and/or to store said parameters on a data carrier. Recording one or more hemodynamic parameters of the hemodynamic parameter set allows evaluation at a later point in time, for example, by medical personnel. Displaying one or more hemodynamic parameters of the hemodynamic parameter set allows diagnostic use by medical personnel, for example.

The hemodynamic parameter set can comprise, as a hemodynamic parameter, a pump rate of the heart and/or the preload of the heart and/or an end-diastolic pressure and/or an end-diastolic volume and/or the afterload of the heart and/or the contractility of the heart and/or a ventricular pressure and/or a ventricular filling volume and/or an atrial pressure and/or an atrial filling volume and/or an arterial pressure and/or a venous pressure.

As already discussed above, said parameters are examples of important hemodynamic parameters or characteristics of heart activity, which means that determining them during operation of the pump system is advantageous both from a diagnostic and from a control engineering point of view.

Concrete examples of determining the hemodynamic parameters of the hemodynamic parameter set based on the time offset and/or the first cannula flow signal and/or the working pressure signal are described further below.

The hemodynamic parameter set can comprise, as a hemodynamic parameter, a pump filling volume and/or an average blood flow as hemodynamic parameters, determined as an average blood flow through the diaphragm fluid pump averaged over a plurality of pumping cycles, and/or a hydrostatic pressure corresponding to a relative position of the diaphragm fluid pump in relation to the heart.

The control unit can be adapted to control the working pressure such that the diaphragm fluid pump is completely filled in the filling phase of each pumping cycle and/or completely emptied in the emptying phase of each pumping cycle.

Complete filling or emptying is understood to mean a complete movement of the diaphragm into the respective end positions. There can be a residual volume of pumping fluid at the end of the emptying phase and a residual volume of working fluid at the end of the filling phase. Complete filling or emptying can prevent the formation of thrombi and/or undersupply of the patient.

It can be provided that the time specification is a specification for the beginning and/or the duration of the filling phase and/or the emptying phase of the first and/or second pumping cycle,
  wherein the hemodynamic parameter set comprises the average blood flow, determined as the average blood flow through the diaphragm fluid pump averaged over a plurality of pumping cycles,
  wherein the control specification is a specification for the hemodynamic parameter set, in particular comprising a specification for the average blood flow, and
  wherein the control unit is further adapted to determine, as a control specification, an increase, decrease or maintenance of the average blood flow based on a time profile of the hemodynamic parameter set.

By controlling the average blood flow according to the control specification determined in this way, a degree of heart support, that is, both the total volume flow of the pulsatile fluid flow generated and the proportion of the pulsatile blood flow in the total blood flow, can be set, with which it is possible to react particularly well to physiological changes and events. In this case, for example, the pump system is particularly suitable for weaning as described above.

The pump system can also have an acceleration sensor and/or yaw rate sensor, adapted for detecting an acceleration signal corresponding to patient activity, the control unit being adapted to determine the control specification based on the acceleration signal, in particular such that the average blood flow is increased with an increase in patient activity.

Since the oxygen requirement and therefore the blood flow requirement depends on patient activity, it is possible in this way to react particularly well to the physiological event of a changed oxygen requirement.

Provision can furthermore be made for the hemodynamic parameter set to comprise, in addition to a contractility of the heart, a preload of the heart and/or an afterload of the heart and the control unit being adapted to
  determine a reduction in the average blood flow as a control specification if the time profile of the hemodynamic parameter set comprises an increase in contractility without an increase in preload and/or without an increase in afterload and/or if the time profile of the hemodynamic parameter set comprises a decrease in preload without a decrease in contractility, and/or
  determine that the average blood flow is kept constant as a control specification if the time profile of the hemodynamic parameter set comprises an increase in contractility and an increase in preload and/or afterload, and/or
  determine an increase in average blood flow as a control specification if the time profile of the hemodynamic parameter set comprises an increase in preload without an increase in contractility and/or if the time profile of the hemodynamic parameter set comprises an increase in afterload without a decrease in preload and without an increase in maximum ventricular pressure and/or if the time profile of the hemodynamic parameter set comprises a decrease in contractility without a decrease in preload and/or without a decrease in afterload.

As already described above, contractility, afterload and preload are important characteristics of cardiac activity and also play a central role in the description of the Frank-Starling mechanism, which describes an important autonomous control circuit of hemodynamics (relationship between filling pressure/filling volume and cardiac output, that is, pumped volume flow per unit of time). A physiologically advantageous control of the mean blood flow and thus of the degree of heart support is achieved by the control unit being adapted for determining the control specification as described above.

The control unit can be adapted to determine the time offset according to the equation $$T = \frac{\tau}{2\pi} \arg\left(\left[\sqrt{\frac{1}{t_1 - t_0} \int_{t_0}^{t_1} Q(t)^2 \, dt} + i \int_{t_S}^{t_E} \left(\frac{Q(t) - \langle Q \rangle}{\sigma_Q}\right)^3 dt\right] e^{i\alpha}\right)$$

where T is the time offset, $\tau$ is a period of the pulsatile fluid flow, Q(t) is a time profile of the first cannula flow signal, t is a time parameter, $t_S$ is the point in time at which Q(t) is less than 20% of $Q_{max}$ for the last time before reaching a maximum flow $Q_{max}$, $t_E$ is the point in time at which Q(t) is less than 20% of $Q_{max}$ at the last time since $Q_{max}$ was reached, $\langle Q \rangle$ is the mean of Q(t) in the time interval from $t_S$ to $t_E$, $\sigma_Q$ is the standard deviation of Q(t) in the time interval from $t_S$ to $t_E$, $t_0$ is the point in time in the middle of the emptying phase of the pumping cycle, $t_1$ is the point in time in the middle of the emptying phase of the following pumping cycle (that is, $t_1-t_0$ is the period duration), i is the imaginary unit, $\alpha$ is a predetermined angular offset. This easily implementable possibility of determining the time offset is explained in more detail below.

The pump system can further comprise
  an ECG sensor adapted to detect an ECG signal corresponding to an electrical activity of the heart,
  and/or a first cannula pressure sensor, adapted for detecting a first cannula pressure signal corresponding to an inlet pressure in the inlet cannula or an outlet pressure in the outlet cannula, the control unit being adapted to determine the time offset and/or the hemodynamic parameter set based on the ECG signal and/or the first cannula pressure signal.

If the pump system comprises an ECG sensor, the point in time at which the emptying phase of a cardiac cycle (for example, the first cardiac cycle) begins, that is, the ventricular systole, and thus a time offset and/or hemodynamic parameters based thereon can be determined particularly reliably and precisely.

For this purpose, the control unit can be adapted to recognize a periodic component of the ECG signal. For example, the control unit can be adapted to recognize a QRS complex as a component of the ECG signal. The control unit can also be adapted to recognize a T-wave and/or a P-wave as a component of the ECG signal. This results in additional information about the time profile of the cardiac cycle or the heart activity, from which in turn time offsets and/or hemodynamic parameters can be determined particularly well.

The pulsatile fluid flow can comprise a measurement phase, the control unit being adapted to set the working pressure to a low working pressure value for the duration of the measurement phase so that a high sensitivity of the first cannula flow signal for pressure changes caused by the first cardiac cycle is achieved.

By providing a measurement phase, the independent reservoir of the diaphragm fluid pump can be used particularly well to determine the time offset and/or hemodynamic parameters.

It can furthermore be provided that the time specification is a specification for the beginning and/or the duration of the filling phase and/or the emptying phase of the first and/or second pumping cycle and that the control specification is a specification for the time offset such that a specified relative phase position of the pulsatile fluid flow in relation to the cardiac activity is achieved, in particular a co-pulse or a counter-pulse or a pulse delayed by a specified delay interval.

A temporal relationship between the pulsatile fluid flow and the cardiac activity is referred to as the relative phase position, that is, a time offset (namely the delay interval) between a point in time by which the pulsatile fluid flow or the working pressure is characterized and a point in time by which the heart activity is characterized. The relative phase offset can exist, for example, only between the filling phases of the pumping cycle and cardiac cycle, only between the emptying phases of pumping cycle and cardiac cycle, between both the filling phases and the emptying phases of pumping cycle and cardiac cycle, or between filling phases of the pumping cycle and emptying phases of the cardiac cycle or between emptying phases of the pumping cycle and filling phases of the cardiac cycle.

The points in time that characterize the definition of the relative phase position of the pulsatile fluid flow and cardiac activity can be the beginning and/or end of filling and/or emptying phases, points in time of maximum and/or minimum flow or other temporal features of the pulsatile fluid flow and the cardiac activity.

A co-pulse is a relative phase position in which a time offset between a point in time of the filling phase of the pumping cycle and a point in time of the filling phase of the cardiac cycle is at least approximately zero and/or in which a time offset between a point in time of the emptying phase of the pumping cycle and a point in time of the emptying phase of the cardiac cycle is at least approximately zero, the filling and/or emptying of the pump and the heart occurring partly or completely at the same time.

A counter-pulse is a relative phase position in which a time offset between a point in time of the filling phase of the pumping cycle and a point in time of the emptying phase of the cardiac cycle is at least approximately zero and/or in which a time offset between a point in time of the emptying phase of the pumping cycle and a point in time of the filling phase of the cardiac cycle is at least approximately zero, the filling of the pump thus occurring at least partially simultaneously with the emptying of the heart and/or the emptying of the pump occurring partially simultaneously with the filling of the heart.

Co-pulse and counter-pulse can thus also be defined as special cases of the specified delay interval, in which the specified delay interval is at least approximately zero.

The relative phase position can be constant over time, at least for a certain time interval, which is the case when the period durations or pump rates of the pulsatile fluid flow and the cardiac activity match. The relative phase position can also change over time, which results from an initially fixed phase position with different period durations or pump rates of the pulsatile fluid flow and the cardiac activity.

By setting the predetermined relative phase position, an advantageous constant or variable relationship between cardiac cycle and pumping cycle can be achieved, which is why setting the predetermined relative phase position is also referred to below as synchronization, although the cardiac cycle and pumping cycle do not actually have to be synchronous. Setting the predetermined relative phase position between the filling and emptying times of the ventricles and the diaphragm fluid pump can also make an important contribution to the targeted loading and unloading of the heart muscle. When the diaphragm fluid pump fills up during the diastole of the heart, the heart muscle does particularly little work, consumes little oxygen and can regenerate. When the blood pump fills up during the systole of the heart, the heart muscle is put under more strain again. Due to the continuous support with a predetermined minimum rate and an emptying time within a permissible range, however, there is no risk of too long stagnation phases in the diaphragm fluid pump or the risk of undersupply to the patient.

The control unit can be adapted to detect a pump rate of the heart and to compare the detected pump rate with a predefined threshold value. The control unit can then also be adapted to abort the synchronization and/or to switch to pumping operation without a predefined relative phase angle if the detected pump rate falls below the predefined threshold value. It can thus be ensured that a sufficient pulsatile fluid flow is provided even if the physiological pump rate of the heart is insufficient.

The control unit can be adapted to achieve the synchronization by means of a fast method, in which the synchronization is still achieved within the first cardiac cycle based on the determined time offset. In order to achieve said synchronization, the control unit can be adapted, upon detecting a change in the first cannula flow signal and/or the first pressure signal and/or upon detecting a periodic component of the ECG signal, to immediately determine the time specification as the predetermined delay interval and to control the working pressure according to the time specification such that the relative phase position is reached in the first heart cycle. The fast method can also be used in (smaller) individual steps over a plurality of pumping cycles. If the time offset is adjusted quickly but over a plurality of pumping cycles, the risk of uneven supply is greatly reduced.

The control unit can also be used to achieve synchronization in other ways, for example, by means of a slower rate variation method compared to the method described above. For this purpose, it can be provided that the control unit is adapted to vary a period of the pulsatile fluid flow over a plurality of pumping cycles, to detect a change in a maximum value and/or minimum value and/or average value and/or instantaneous value and/or another time profile feature (such as a skewness) of the first cannula flow signal, which is caused by varying the period duration and determined per pumping cycle and to determine the time specification such that the maximum value and/or minimum value and/or average value and/or instantaneous value of the first cannula flow signal determined per pumping cycle is maximized or minimized.

If, in this rate variation method, the first cannula flow signal corresponds approximately to the inlet flow and the time specification is determined such that the maximum value of the first cannula flow signal is maximized, then a counter-pulse is achieved as the relative phase position; if, on the other hand, the maximum value of the first cannula flow signal is minimized, a co-pulse is achieved as the relative phase position. The rate variation method allows a particularly gentle synchronization with few side effects.

It can be provided that the control specification is a specification for the time offset and that the control unit is adapted to change the period of the pulsatile fluid flow over a plurality of pumping cycles in a first direction when a deviation of the time offset determined by the control unit from the control specification is detected, until a sign change of a derivative of a maximum value and/or minimum value and/or mean value and/or instantaneous value and/or another time profile feature of the first cannula flow signal determined per pumping cycle is detected, and is further adapted to change the period of the pulsatile fluid flow in the direction opposite to the first direction when the change of sign is detected.

A particularly stable and precise synchronization can be achieved in this way (in particular by regularly repeating the method), the control unit being able to react well to physiological changes.

The control unit can be adapted to determine a pressure and/or a pressure change and/or a pressure change rate in a ventricle and/or atrium and/or blood vessel connected to the diaphragm fluid pump based on a time profile of the first cannula flow signal.

This is made possible by the fact that the flows relevant for the first cannula flow signal are influenced by pressures in the associated ventricles or atria or blood vessels. In this way, important pressure variables and their profiles can also be estimated without correspondingly placed pressure sensors or, if such pressure sensors are present, additional information can be obtained. For example, based on the time profile of the inlet flow, an increase in the pressure in a ventricle or a blood vessel, for example, also in one or two vena cavae connected to the diaphragm fluid pump, can be detected and/or the pressure in the vena cavae can be estimated (the latter can be important, for example, in failing Fontan patients).

Furthermore, the heart support system can be adapted to determine at least one position parameter of a patient. The control unit can be adapted to calculate an additional pressure caused by a liquid column in the inlet cannula and/or the outlet cannula for determining the position parameter.

The heart support system can have a sensor adapted for determining the position parameter, for example, a gyroscopic sensor.

Determining a pressure and/or a pressure change and/or a pressure change rate in a ventricle and/or atrium and/or blood vessel connected to the diaphragm fluid pump can be promoted by positioning the diaphragm fluid pump near or at the level of the so-called (venous) hydrodynamic point of indifference (HIP), for which purpose the determination of the at least one position parameter can be useful. At low filling pressures, the flow is particularly dependent on the pressure at the proximal end of the inlet cannula. Due to the positioning of the diaphragm fluid pump at the level of the HIP, the position of the patient has no influence on the determination of the pressure and/or the pressure change and/or the rate of pressure change. If it is not possible to position the diaphragm fluid pump at the level of the HIP, the determined position parameter of the patient can thus also be incorporated when determining the pressure etc.

The control unit can be adapted to change the period of the pulsatile blood flow when detecting a change in pressure in a blood vessel connected to the diaphragm fluid pump such that the detected change in pressure is partially or completely compensated.

The control unit can be adapted to vary the time offset by varying the time specification over a plurality of pumping cycles such that the pressure and/or the pressure change and/or the pressure change rate in the ventricle and/or atrium and/or blood vessel connected to the diaphragm fluid pump can be determined based on a change in the time profile of the first cannula flow signal caused by varying the time offset.

In this way, the additional reservoir, which is provided by the diaphragm fluid pump in the blood circuit, can in turn be used particularly well for a measurement.

The hemodynamic parameter set can comprise an instantaneous fill level of the diaphragm fluid pump, determined based on an integral of the first cannula flow signal, the control unit being adapted to compare the instantaneous fill level with a time-varying instantaneous setpoint fill level of the diaphragm fluid pump and, if the instantaneous fill level falls below the instantaneous setpoint fill level by at least a predetermined value, to control the working pressure such that a pump rate of the pulsatile fluid flow and/or a suction pressure, with which the diaphragm fluid pump is filled, is reduced.

The instantaneous setpoint fill level is typically a function that changes over time and specifies a setpoint fill level for the diaphragm fluid pump at any point in time. If the instantaneous fill level falls below the instantaneous setpoint fill level by at least the specified value, then this is an indication of a physiological event that reduces the inlet flow rate. Such a physiological event can be suction of a heart wall or a collapse of a vena cava (the latter is particularly important in failing Fontan patients); reducing the pump rate or the suction pressure counteracts such an event.

A possible disadvantage of this method is that the pump rate or suction pressure can be reduced too much over time.

In order to prevent this, the control unit can further be adapted to increase the pump rate of the pulsatile fluid flow and/or the suction pressure over a plurality of pumping cycles until the instantaneous fill level falls below the instantaneous setpoint fill level by at least the specified value, and to then reduce the pump rate of the pulsatile fluid flow and/or the suction pressure.

In this way, events such as the suction of the heart wall or the collapse of vena cavae can be avoided without excessively reducing the pump rate of the pulsatile fluid flow or the suction pressure.

The control unit can be adapted, if a drop in pressure is detected in a blood vessel connected to the diaphragm fluid pump, to check whether there is an indication that said blood vessel is collapsing (where the indication can be, for example, that in the example described above, the instantaneous fill level falls below the instantaneous setpoint fill level by at least the specified value). The pressure in said blood vessel can in particular be a central venous pressure (CVP). Furthermore, the control unit can then be adapted, if such an indication is not present, to reduce the duration of the emptying phase of the pumping cycle (specified, for example, as a fraction of the systole duration of the cardiac cycle), to increase the suction pressure with which the diaphragm fluid pump is filled, and to decrease the pump rate of the pulsatile fluid flow. Said steps can in particular be carried out in the order mentioned.

Complete filling of the diaphragm fluid pump can be ensured in this way. A reaction to a drop in CVP is particularly important in failing Fontan patients.

Also, if such an indication is present, the control unit can be adapted to reduce the duration of the emptying phase of the pumping cycle, then to reduce the suction pressure with which the diaphragm fluid pump is filled and to reduce the pump rate of the pulsatile fluid flow. Said steps can in particular be carried out in the order mentioned.

In this way, a collapse of the blood vessel can be prevented/reduced when the diaphragm fluid pump is completely filled. A reaction to a drop in CVP is particularly important in failing Fontan patients.

The pump system can further comprise a second diaphragm fluid pump, which can also be fluidically connected to the heart and/or at least one blood vessel connected to the heart and is adapted for generating a pulsatile fluid flow for supporting a cardiac activity of the heart and is further connected by means of a pressure line to the working pressure source or a second working pressure source, the control unit for controlling the second diaphragm fluid pump being able to be adapted in the same way as for controlling the first diaphragm fluid pump.

The pump system, which comprises two diaphragm fluid pumps, is particularly suitable as a biventricular VAD (BVAD), which means that the advantages of the pump system are also available for patients who need a BVAD.

The pump system can be designed as a stationary or mobile system.

The proposed control unit is intended for use with the proposed pump system. The control unit is therefore adapted for controlling the working pressure and further to determine the time offset,
to determine the hemodynamic parameter set based on the time offset and/or the first cannula flow signal and/or the working pressure signal and
to determine the time offset based on the control specification such that the control specification is achieved.

The control unit can be adapted for use with different diaphragm fluid pumps and/or working pressure sources, for example, diaphragm fluid pumps of different sizes (that is, in particular with different filling volumes) and/or working pressure sources, optionally comprising a piston pump or a pneumatic circuit.

The control unit can be designed as an independent unit, or it can be provided, for example, as an upgradeable software component of an existing control unit, a mobile data processing device and/or a workstation computer.

The control unit can be developed according to the features mentioned above in connection with the pump system.

The proposed method for operating a pump system of the type described above comprises the steps:
detecting the first cannula flow signal and the working pressure signal,
determining the time offset and/or the emptying time offset for the first pumping cycle and the first cardiac cycle,
determining the hemodynamic parameter set based on the time offset and/or the first cannula flow signal and/or the working pressure signal,
determining the time specification based on the control specification such that the control specification is achieved.

The method thus represents an advantageous use of the pump system described. Depending on the nature of the pump system and the requirements of pump use, the method can comprise further steps which can result, for example, from the features mentioned above in connection with the pump system.

Embodiments of the described pump system and the described method for operating a pump system are explained below with reference to FIG. 1 to FIG. 10. Various essential or also advantageous further developing elements are mentioned in each case within the framework of a specific example, whereby individual of these elements can also be used as such for developing the pump system, the control unit and/or the method—also detached from the context of the respective example and further features of the respective example.

Recurring and similar features of different embodiments are identified in the figures and the following description in each case with the same reference numbers, with the reference numbers being partially omitted if the identified features are not mentioned in relation to a specific drawing.

The pump system 1 shown in FIG. 1 comprises a diaphragm fluid pump 2, a working pressure source 3 and a control unit 4.

The diaphragm fluid pump 2 comprises a housing 5, in the interior of which a cavity is formed, which cavity is divided by a deflectable diaphragm 6 into a pump fluid chamber 7 and a working fluid chamber 8.

The pump fluid chamber 7 has a fluid inlet 10 connected to an inlet cannula 9 and a fluid outlet 12 connected to an outlet cannula 11.

The working fluid chamber 8 can be filled with air as the working fluid and is connected to the working pressure source 3 by means of a pressure line 15 that, by means of the working pressure source 3, an overpressure and/or a negative pressure can be generated in the working fluid chamber 8 for deflecting the diaphragm 6, whereby the working pressure source 3 is thus is adapted for providing a working pressure for driving the diaphragm fluid pump 2.

In the example, the working pressure source 3 is a piston pump, comprising a working piston 18 that can be moved in a working chamber 16 and is driven by an electric motor 17. The working pressure source 3 can alternatively be another type of pump or a pneumatic circuit, for example, a pneumatic circuit comprising a compressor, a positive pressure tank and a negative pressure tank. The working fluid can also be another gas or a liquid.

The control unit 4 is adapted for controlling the working pressure. For this purpose, said control unit is connected to the motor 17 of the working pressure source 3 via a control line 19. The pump system 1 comprises further lines, such as control and communication lines, for example, between the control unit 4 and the various sensors, which are not shown for the sake of simplicity.

A working pressure sensor 20 is arranged on the pressure line 15 and is adapted for detecting a working pressure signal corresponding to the working pressure in the pressure line 15.

The working pressure signal detected by means of the working pressure sensor 20 is used by the control unit 4 as a monitoring and feedback signal for controlling the working pressure and thus the pulsatile fluid flow.

The diaphragm fluid pump 2 comprises an inlet valve 13 arranged in the fluid inlet 10 and an outlet valve 14 arranged in the fluid outlet 12. The valves 13 and 14 are one-way valves, so that without an active control, a fluid can only flow in through the inlet 10 and only flow out through the outlet 12. Alternatively, the inlet valve 13 and/or the outlet valve 14 can be actuated valves which can be controlled by the control device 4 such that the fluid can flow in through the inlet 10 and out through the outlet 12 during operation.

The diaphragm fluid pump 2 can be fluidically connected to a heart and/or at least one blood vessel connected to the heart by means of the inlet cannula 9 and the outlet cannula 11. For example, the inlet cannula 9 can be connected to a left ventricle of the heart, the outlet cannula 11 can be connected to an aorta, whereby the pump system can be used as a left-sided VAD (LVAD). Alternatively, the inlet cannula 9 can be connected, for example, to a right ventricle of the heart, the outlet cannula 11 can be connected to a pulmonary artery, whereby the pump system can be used as a right-hand VAD (RVAD). For example, for the treatment of failing Fontan patients, the inlet cannula can be connected to at least one vena cava and the outlet cannula can be connected to a pulmonary artery.

The pump system 1 has a first flow sensor 21 and a second flow sensor 22. The first flow sensor 21 is arranged on the inlet cannula 9 and adapted for detecting a first cannula flow signal corresponding to an inlet flow in the inlet cannula 9. The second flow sensor 22 is arranged on the outlet cannula 11 and adapted for detecting a second cannula flow signal corresponding to an outlet flow in the outlet cannula 11. The first flow sensor 21 and the second flow sensor 22 are ultrasonic flow sensors, but can also be other types of flow sensors, for example, Hall effect sensors. The pump system 1 can also only have a single flow sensor, which can be arranged, for example, on the inlet cannula 9 or on the outlet cannula 11, or said pump system can have more than two flow sensors at different points of the region through which the blood flows.

The diaphragm fluid pump 2 is adapted for generating a pulsatile fluid flow for supporting a cardiac activity of the heart. The pulsatile fluid flow is generated by deflecting the diaphragm 6 in opposite directions.

Here, in each pumping cycle, a negative pressure is first generated in the working fluid chamber 8 by means of the working pressure source 3, in which the working chamber 16 is enlarged by moving the working piston 18 by means of the electric motor 17. Here, the outlet valve 14 closes, the inlet valve 13 opens. Due to the negative pressure and the open inlet valve 13, blood flows through the fluid inlet 10 into the pump fluid chamber 7 (filling phase). If this is filled, that is, If the diaphragm 6 is in a first end position, an overpressure is generated in the working pressure source 3 (by moving the working piston 18 in an opposite direction), the inlet valve 13 closes and the outlet valve 14 opens, so that blood is displaced from the pump fluid chamber 7 through the outlet 12 (emptying phase) until the pump fluid chamber 7 is emptied. (The end position of the diaphragm 6 can be detected, for example, by means of an integral of the first cannula flow signal and/or based on a flattening of the first cannula flow signal and/or can be ensured by various control methods—see the publication EP 3 536 955 A1.)

The next pumping cycle can then begin. The beginning and duration of the filling phase and the emptying phase are each determined by the control unit 4 as a time specification (examples of this are described further below). According to said time specification, a phase with a working pressure that lies between the filling and the emptying pressure (for increasing the measuring sensitivity), for example, the measurement phase mentioned above, can be provided between the successive filling and emptying phases.

The pump system 1 further comprises ECG sensors 23, adapted for detecting an ECG signal corresponding to an electrical activity of the heart, a first cannula pressure sensor 24, adapted for detecting a first cannula pressure signal corresponding to an inlet pressure in the inlet cannula 9, and a second cannula pressure sensor 25, adapted for detecting a second cannula pressure signal corresponding to an outlet pressure in the outlet cannula 11. The pump system 1 can, for example, also have only a single cannula pressure sensor, which can be arranged, for example, on the inlet cannula 9 or on the outlet cannula 11.

The control unit 4 further has a display unit 26 adapted to display various system parameters, suggested settings, hemodynamic parameters and control options.

The diaphragm fluid pump 2 further comprises an acceleration sensor 27, adapted for detecting an acceleration signal corresponding to patient activity.

The control unit 4 is adapted to determine a time offset between a first point in time, which occurs during a first pumping cycle, and a second point in time, which occurs during a first cardiac cycle. Determining the time offset is described below using various examples. Here, in the various examples, different sensor signals are used to determine the time offset. The control unit 4 can be adapted for determining the time offset, for example, according to one or more of the examples (also depending on which sensors the pump system 1 has, for example, in different embodiments) and can alternatively or additionally also be adapted to determine the time offset in a different way or based on other sensor signals.

In a first example, the time offset is determined based on the first cannula flow signal corresponding to the inlet flow time profile Q(t). To illustrate this example, an exemplary inlet flow profile Q(t) in the inlet 10 of the diaphragm fluid pump 2 and an exemplary ventricular pressure profile $p_{LV}(t)$ of a ventricle connected to the diaphragm fluid pump 2 were calculated by a first simulation of the pump system 1. The first simulation is based on the following parameters and assumptions: If the complete filling volume of the connected diaphragm fluid pump 2 has been withdrawn from the ventricle, it only builds up half the pressure that it would build up without withdrawing the filling volume. The time profile of the pressure build-up and drop are approximated by the scaled cosine function. The systole lasts 50% of the heartbeat. The rise in pressure lasts 70% of the systole. The working pressure has a trapezoidal profile over time. The filling volume is 80 ml, the ventricular pressure varies with a maximum pressure change rate of 10 to 120 mmHg/s, the aortic pressure is 100 mmHg, the heart rate is 78 bpm, the pump rate is 82 bpm.

Figure 2:
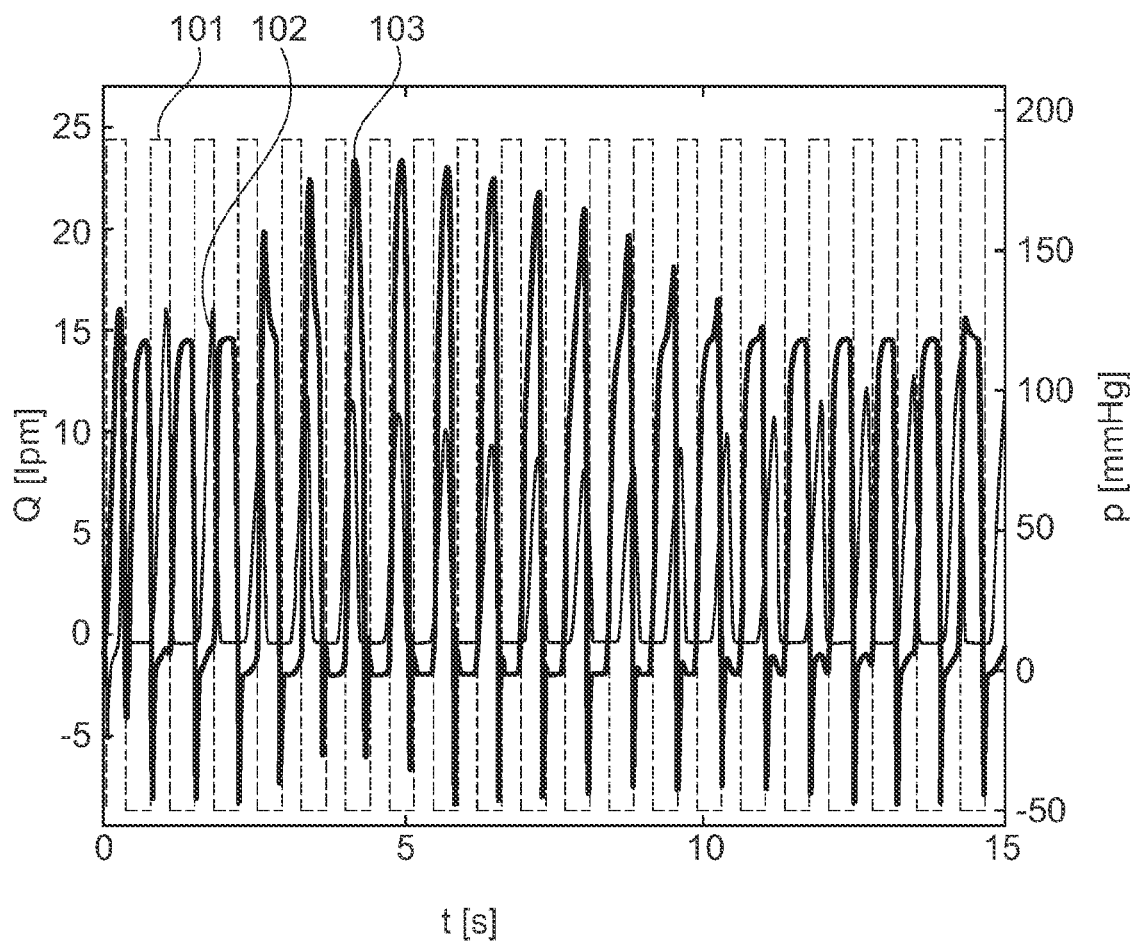
FIG. 2 is a graphical representation of results of a first simulation.

The graph in FIG. 2 shows exemplary time profiles of the first simulation. Curve 101 shows the working pressure time profile $p_A(t)$, curve 102 the ventricular pressure time profile $p_{LV}(t)$, curve 103 the inlet flow time profile Q(t). It can be seen here that the inlet flow is increased when the systole takes place during the filling phase of the diaphragm fluid pump 2 (the time offset between curves 102 and 103 shifts due to the difference between heart rate and pump rate as a function of time t.) The pressure build-up through the ventricle decreases when the ventricular volume is reduced in systole.

Figure 3:
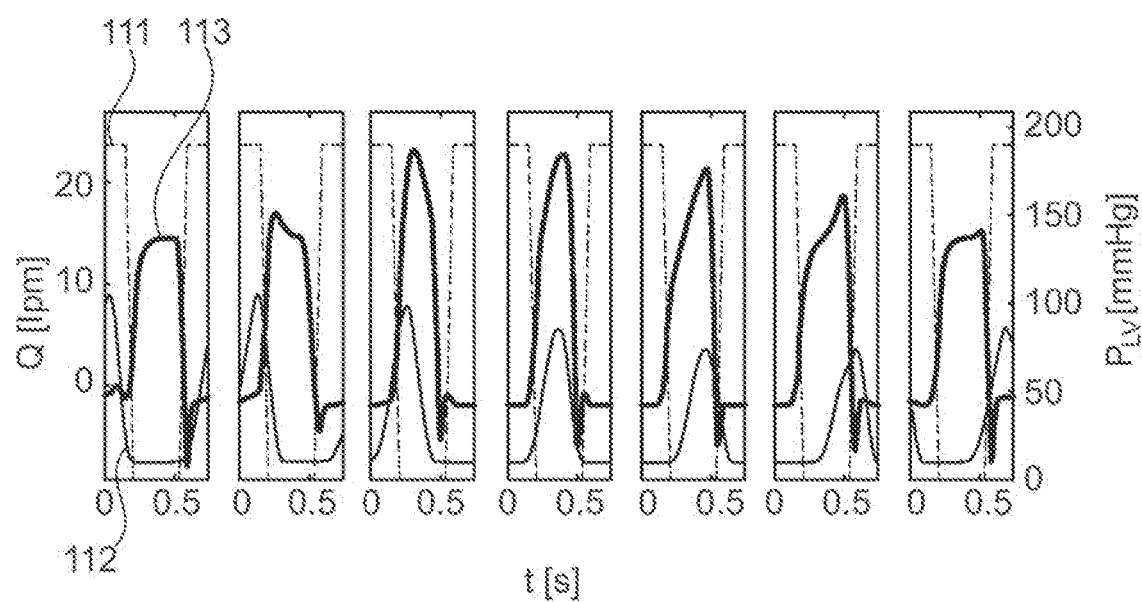
FIG. 3 is a graphical representation of further results of the first simulation.

To clarify the determination of the time offset, simulated data like that shown in FIG. 2 was divided into seven groups. Each group corresponds to an equal region of the time offset. In the first group, the maximum ventricular peak pressure is well before the middle of the filling phase. In the middle group, the two points in time coincide. The seven individual graphs in FIG. 3 show the average values formed in the groups over the working pressure time profile (curves 111), the ventricular pressure time profile (curves 112) and the inlet flow time profile (curves 113) from the first simulation.

The curves 113 show how the shape of the inlet flow profile changes when the time offset changes. For a quantitative determination of the time offset, the skewness of the inlet flow profile is first calculated according to the equation $$s = \int_{t_S}^{t_E} \left( \frac{Q(t) - \langle Q \rangle}{\sigma_Q} \right)^3 dt$$

where s is the skewness, Q(t) is the inlet flow time profile, t is a time parameter, $t_S$ is the point in time at which Q(t) is less than 20% of $Q_{max}$ for the last time before reaching a maximum flow $Q_{max}$, $t_E$ is the point in time when Q(t) is less than 20% of $Q_{max}$ for the last time since reaching $Q_{max}$, $\langle Q \rangle$ is the average of Q(t) in the time interval from $t_S$ to $t_E$, $\sigma_Q$ is the standard deviation of Q(t) in the time interval from $t_S$ to $t_E$. Furthermore, the root mean square r of the inlet flow profile in the time interval from $t_S$ to $t_E$ is calculated as $$r = \sqrt{\frac{1}{t_1 - t_0} \int_{t_0}^{t_1} Q(t)^2 dt}$$

Figure 4:
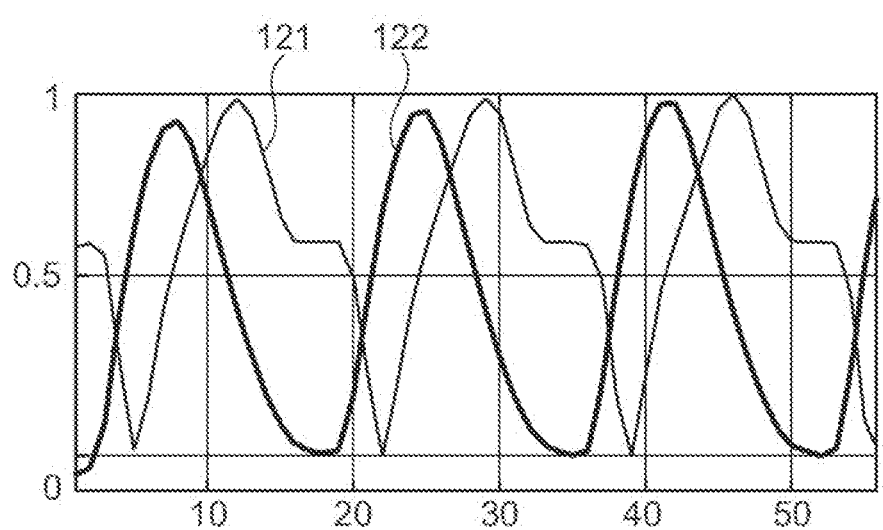
FIG. 4 is a graphical representation of further results of the first simulation.

FIG. 4 shows a time profile of the skewness s (curve 121) and the root mean square r (curve 122) over a plurality of pumping cycles (x-axis) of the first simulation, with r and s normalized to the interval from 0 to 1 for better representation.

For further calculation, a complex number c is defined as c=r+i s, where i is the imaginary unit. A relative phase position p between the pumping cycle and the cardiac cycle can then be estimated as p=arg(c) or p=arg(c·$e^{i\alpha}$), where the optional multiplication by $e^{i\alpha}$ only shifts the phase by a desired angular offset α.

Figure 5:
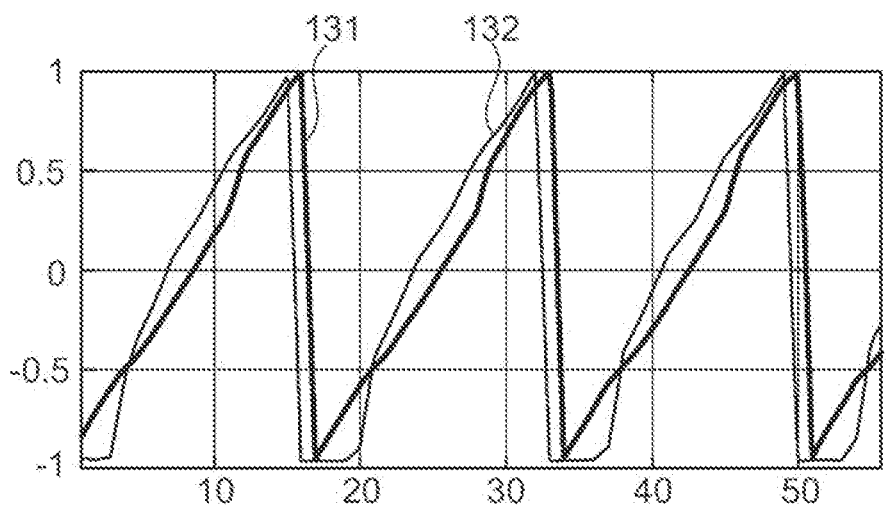
FIG. 5 is a graphical representation of further results of the first simulation.

FIG. 5 shows a time profile of the actual relative phase position according to the simulation (curve 131) and the relative phase position (curve 132) determined as p=arg (c·$e^{i\alpha}$), in each case normalized to the interval from −1 to 1 by dividing by the circular number n over a plurality of pumping cycles (x-axis) of the first simulation. From the relative phase position p/π normalized in this way, the time offset T can be estimated as T=p·τ/2π, where τ is the period of the pulsatile fluid flow. So, in summary, T is given as $$T = \frac{\tau}{2\pi} \arg\left( \left[ \frac{1}{t_1 - t_9} \int_{t_0}^{t_1} Q(t)^2 \, dt + i \int_{t_S}^{t_E} \left( \frac{Q(t) - \langle Q \rangle}{\sigma_Q} \right)^3 dt \right] e^{i\alpha} \right).$$

FIG. 5 shows that the determination of the time offset provides good results over a wide range. The determination is only inaccurate in the region of the plateau of the characteristics r and s, which can be seen in FIG. 4, since the inlet flow is insensitive to changes in the phase position here. The control unit 4 can be adapted to set the time specification such that a relative phase position that is favorable for determining the time offset is achieved at least temporarily, in particular such that the beginning or the end of the emptying phase of the first cardiac cycle occurs during the filling phase of the first pumping cycle. The aforementioned insensitivity can be circumvented In this way.

In a second example, the time offset is also determined based on the first cannula flow signal corresponding to the inlet flow time profile Q(t). In the first example, the time offset could be determined from two characteristics of the inlet flow time profile, s and r. As can be seen from FIG. 4, looking at just one of the two variables would still not allow the phase position to be determined unambiguously, since each value of s and r occurs at two different phase positions. However, the control unit 4 can be adapted to vary the pump rate or period duration over a plurality of pumping cycles, so that the sign of the derivative of r and/or s can be determined, which also enables the phase position and thus the time offset to be determined unambiguously.

Figure 6A:
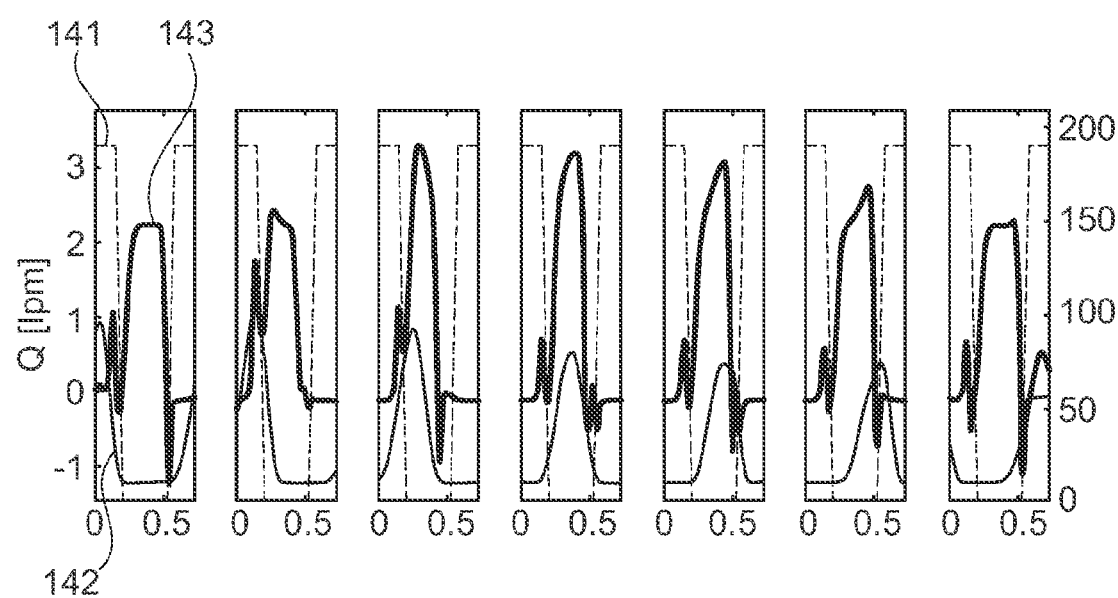
FIG. 6a is a graphical representation of results of a second simulation.
Figure 6B:
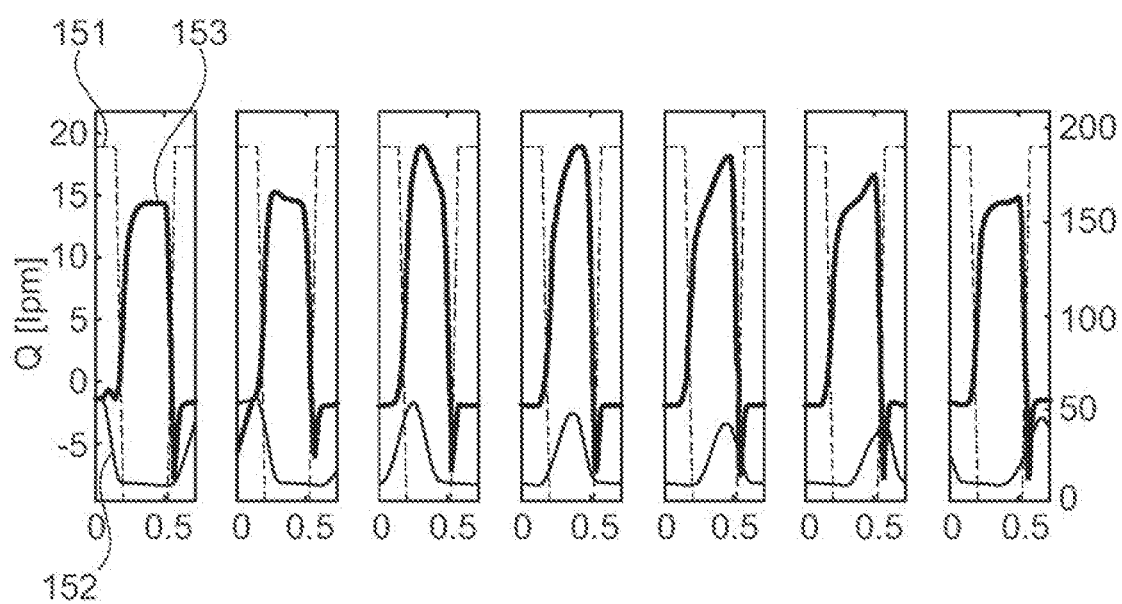
FIG. 6b is a graphical representation of results of a third simulation.
Figure 6C:
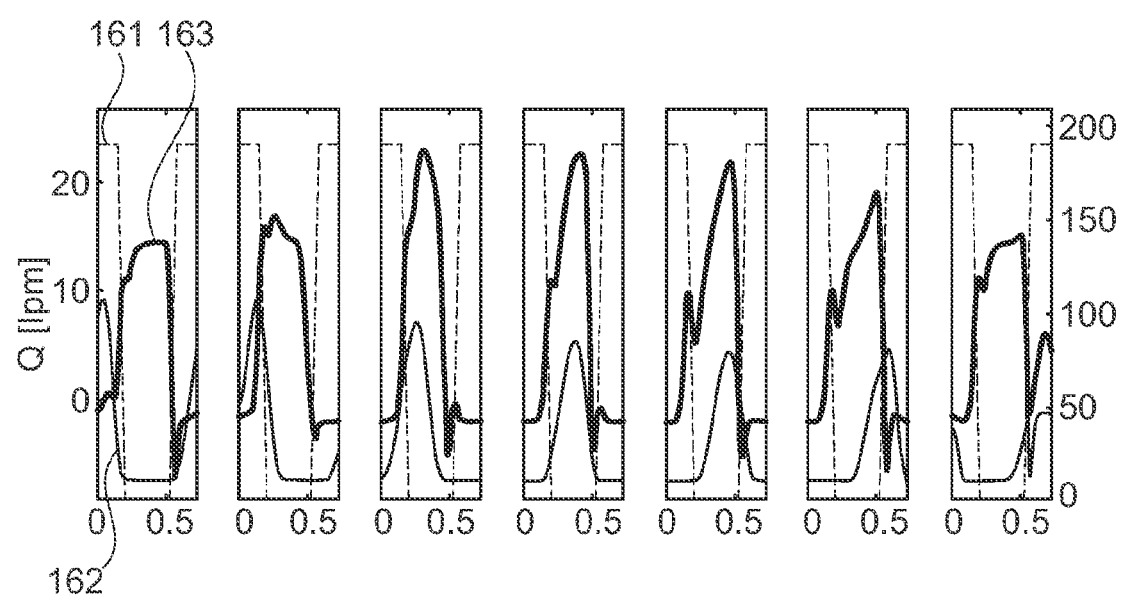
FIG. 6c is a graphical representation of results of a fourth simulation.

FIGS. 6a to 6c show the results of further simulations, the procedure, assumptions and parameters of which correspond to the first simulation apart from the deviations mentioned below, which are used to check whether load changes and other parameter changes interfere with the determination of the phase position.

FIG. 6a shows the averaged time profiles (over seven groups formed analogously to FIG. 3) of working pressure (curves 141), ventricular pressure (curves 142) and inlet flow (curves 143) of a second simulation. The filling volume here is 10 ml, the heart rate is 75 bpm.

FIG. 6b shows the averaged time profiles (over seven groups formed analogously to FIG. 3) of working pressure (curves 151), ventricular pressure (curves 152) and inlet flow (curves 153) of a third simulation. The ventricular pressure here varies with a maximum rate of pressure change of 8 to 60 mmHg/s.

FIG. 6c shows the averaged time profiles (over seven groups formed analogously to FIG. 3) of working pressure (curves 161), ventricular pressure (curves 162) and inlet flow (curves 163) of a fourth simulation. The aortic pressure here is 70 mmHg.

In FIGS. 6a-6c, it is easy to see that the dependency of the inlet flow curves on the phase position is qualitatively similar to that in FIG. 3. The formalism given above is also applicable here. The method is therefore robust with respect to load changes. However, it can be advantageous to re-normalize or calibrate the variables s and r for each parameter set in order to minimize deviations. During operation, it is also possible to repeat the calibration regularly in order to continue to reliably synchronize even after large load changes. The mapping to the phase position can also be determined in a different way than described above, for example, by means of a neural network, for which the flow curves according to FIG. 3 and FIGS. 6a-6c could serve as inputs and the phase position as output.

In a third example, the time offset is determined based on the ECG signal. The control unit 4 is adapted to recognize a QRS complex as a component of the ECG signal. This corresponds to the beginning of the emptying phase of the first cardiac cycle. Since the beginning of the emptying phase of the first pumping cycle is known, the time offset can be determined directly as an emptying time offset. The control unit 4 can additionally or alternatively be adapted for recognizing a T-wave and/or a P-wave as a component of the ECG signal.

The control unit 4 is further adapted to determine a hemodynamic parameter set, comprising a plurality of hemodynamic parameters, based on the time offset and/or the first cannula flow signal and/or the working pressure signal. The determination of hemodynamic parameters is described below using various examples. Here, in the various examples, different sensor signals are used for determining different hemodynamic parameters of the hemodynamic parameter set. The control unit 4 can be adapted for determining hemodynamic parameters, for example, according to one or more of the examples (also depending on which sensors the pump system 1 has, for example, in different embodiments) and can alternatively or additionally also be adapted to determine the same or other hemodynamic parameters in a different way or based on other sensor signals.

In a first example, various hemodynamic parameters are determined based on the first cannula flow signal and/or the second cannula flow signal. The period of the pulsatile fluid flow here is initially set such that a continuously changing relative phase position occurs (similar to the first simulation, see FIG. 2). The contractility can then be determined as the maximum value of the first cannula flow signal per pumping cycle, the preload as the minimum value of the first cannula flow signal per pumping cycle, the afterload as the maximum value of the second cannula flow signal per pumping cycle. Said maximum and minimum values can be weak, heavily distorted or noisy signals. The control unit 4 can be adapted to determine temporal average values over a longer period of time, for example, overnight, for better determining of weak, heavily distorted or noisy signals, that is, to carry out a long-term averaging. The long-term averaging overnight is advantageous because, in this way, the position of the diaphragm fluid pump in relation to the heart/circulatory system of the patient is kept relatively constant. Alternatively or additionally to the measurement overnight, the control unit 4 can be adapted for determining at least one position parameter of a patient (for example, as described above) and for correcting the long-term averaging based on the position parameter.

In a second example, as in the first example, various hemodynamic parameters are determined based on the first cannula flow signal and/or the second cannula flow signal, but additionally also based on the ECG signal. Here, the ECG signal is used to precisely detect the first and/or second cannula flow signal during the diastole and/or the systole of the cardiac cycle. In this example too, the control unit 4 can and should be adapted for carrying out a long-term averaging and/or for correcting the long-term averaging on the basis of the position parameter.

In a third example, various hemodynamic parameters are determined based on the first and second cannula flow signals and the ECG signal. This exploits the fact that a precise delay in the filling phase or the emptying phase of the pulsatile fluid flow can be set based on the EKG signal. In a first step, the beginning of the filling phase of the pulsatile fluid flow is gradually delayed over a plurality of pumping cycles with respect to the beginning of the filling phase of the heart activity. With the information obtained in this way, a calibration can first be carried out, in which the working pressure is adapted to the position of the diaphragm fluid pump 2. For this purpose, for example, the emptying pressure is set such that the resulting profile of the second cannula flow signal corresponds to a previously stored profile of the second cannula flow signal at a minimum aortic pressure. After calibration, it is possible to determine a rate of change of the first cannula flow signal in systole as a measure of contractility. A curve shape of the aortic pressure can be determined from the variation of the second cannula flow signal, from which in turn an opening time of the aortic valve (as the duration for the pressure build-up), a circulatory resistance (as the duration for the pressure reduction) and the contractility (as the slope of the pressure build-up) can be determined.

Figure 7:
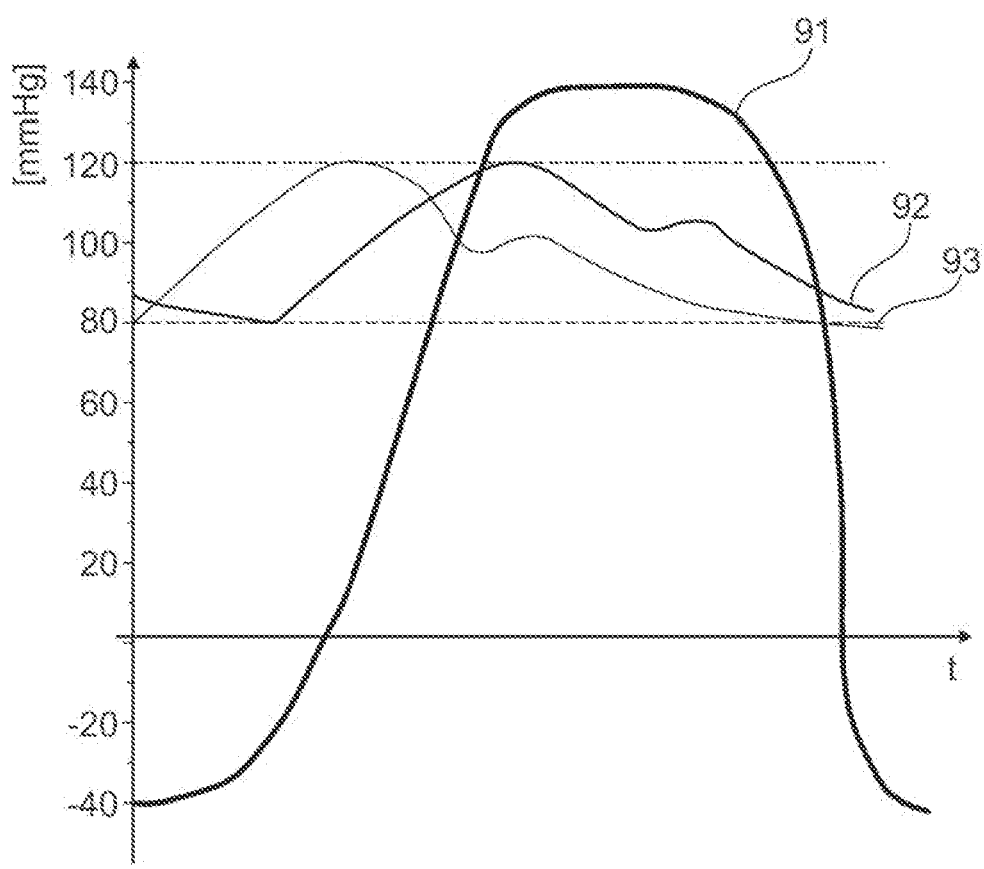
FIG. 7 is a schematic representation of an example of determining hemodynamic parameters.

For this type of parameter determination, FIG. 7 shows an example of the time profile of the pump pressure (curve 91), the aortic pressure for a first delay (curve 92) and the aortic pressure for a second delay (curve 93). The measured second cannula flow signal begins when the pump pressure is greater than the aortic pressure, which is why the aortic pressure can be approximately determined by recording a plurality of measured values of the second cannula flow signal.

In a fourth example, various hemodynamic parameters are determined based on the first cannula pressure signal. The preload is determined as end-diastolic pressure. Contractility is determined from a volume dependent rate of change in systolic pressure. The afterload is determined as the maximum pressure determined over a cardiac cycle.

The control unit 4 is further adapted, based on a control specification as a specification for the hemodynamic parameter set and/or for the time offset, to determine a time specification as a specification for a beginning and/or a duration of the filling phase and/or the emptying phase of the first pumping cycle and/or a second pumping cycle, which occurs temporally after the first pumping cycle, such that the control specification is achieved.

The control unit 4 is adapted to control the working pressure based on the time specification such that the control specification is achieved. Alternatively or additionally, the display unit 26 can be configured for displaying a proposed setting change determined based on the time specification, which setting change can then be selected by the patient or medical personnel.

The control specification can have different control goals. A possible control goal is to adapt the degree of cardiac support, in particular the average blood flow through the diaphragm fluid pump averaged over a plurality of pumping cycles, to physiological changes or events, as described above.

The further control goal of the synchronization, that is, the setting of a predefined relative phase position of the pulsatile fluid flow in relation to the cardiac activity, is described below using various examples.

In the synchronization, it is provided in any case that the time specification is a specification for the beginning and/or the duration of the filling phase and/or the emptying phase of the first and/or second pumping cycle and that the control specification is a specification for the time offset such that the predetermined relative phase position of the pulsatile fluid flow in relation to the cardiac activity is reached.

In a first example, the control unit 4 is adapted for achieving the synchronization based on the first cannula flow signal by means of a fast method, in which the synchronization is still achieved within the first cardiac cycle based on the time offset determined.

Figure 8:
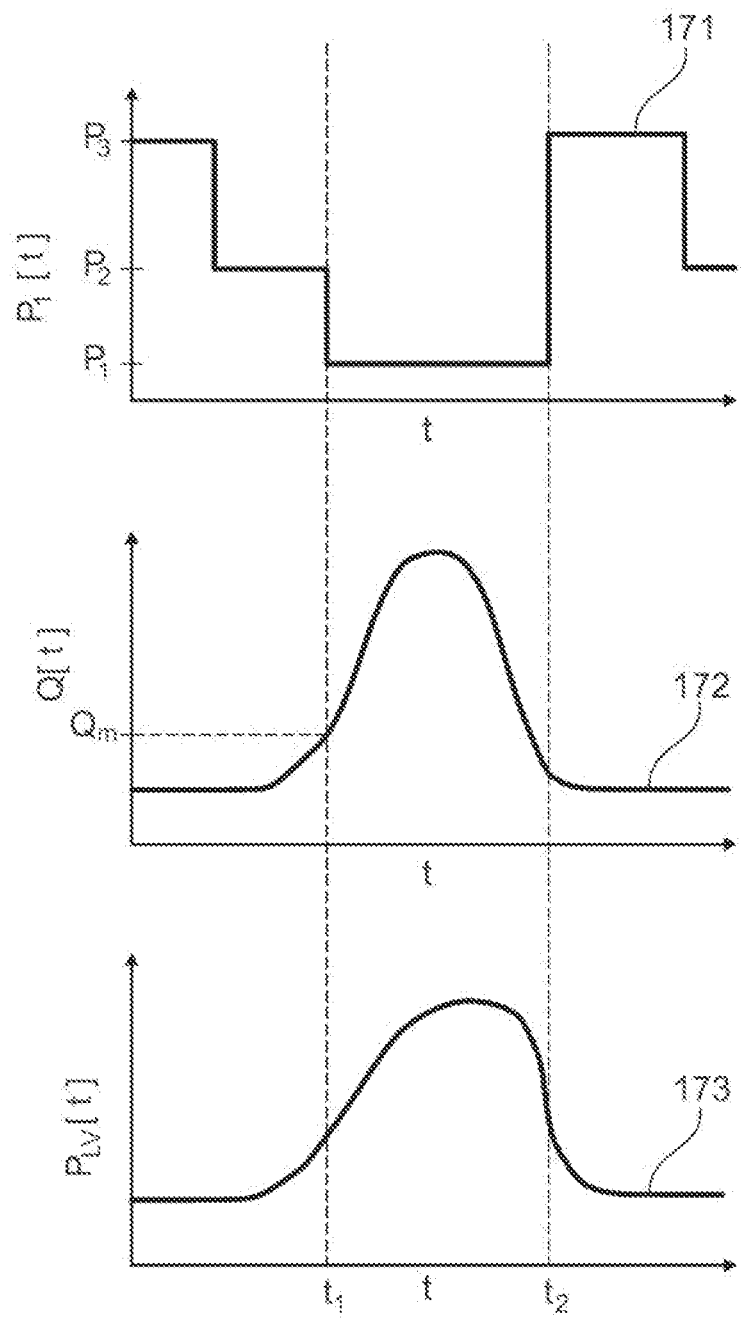
FIG. 8 is a schematic representation of a first example of a synchronization.
Figure 9:
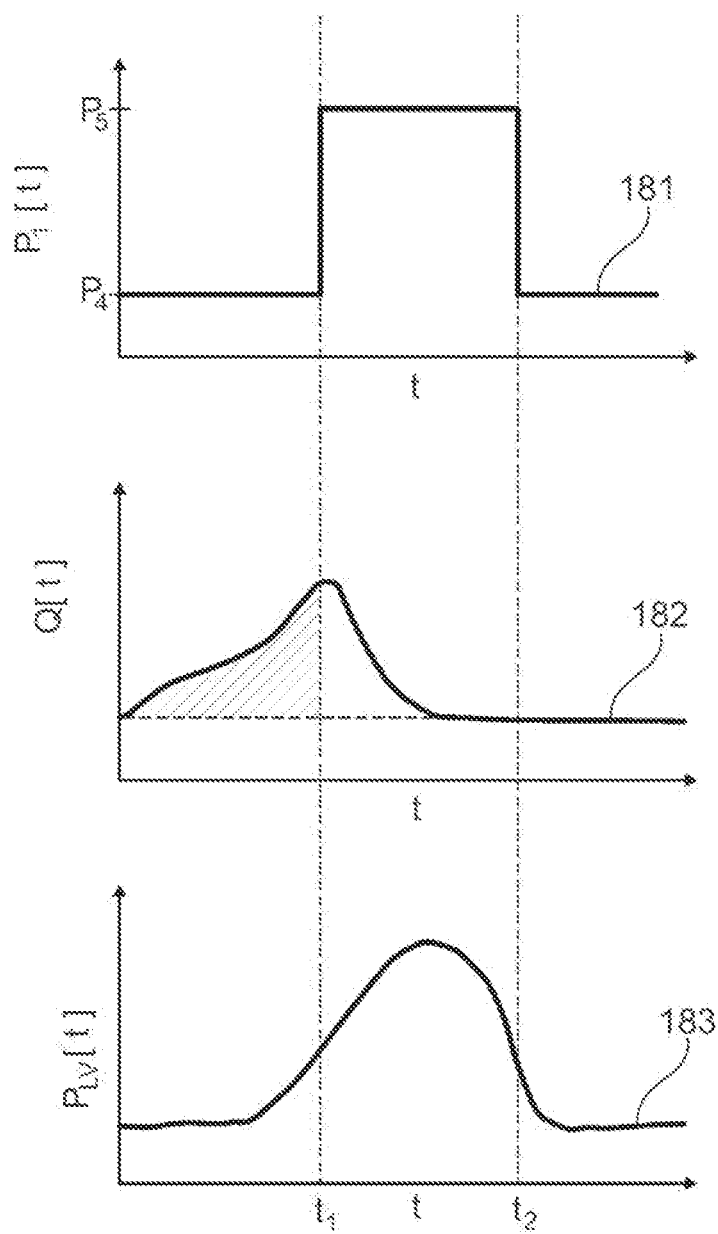
FIG. 9 is a schematic representation of a second example of a synchronization.

This type of synchronization is illustrated in FIG. 8, a counter-pulse being set as the relative phase position. FIG. 8 shows the time profiles of the working pressure $p_A(t)$ (curve 171), the first cannula flow signal Q(t) (curve 172) and the ventricular pressure $p_{LV}(t)$ in the left ventricle (curve 173).

First, a working pressure $p_2$ is set that is slightly above the inlet pressure in diastole. The beginning of the systole is detected in the first cannula flow signal as a flow limit value $Q_m$ being exceeded. At this point in time ($t_1$), the working pressure is controlled to a lower suction pressure $p_1$ until the pump fluid chamber 7 is filled (point in time $t_2$). Then there is a changeover to an emptying pressure $p_3$. The counter-pulse set in this way has, among other things, the property that suction events are avoided.

A delayed co-pulse is set in a modification of the first example. This type of synchronization is illustrated in FIG. 9, wherein again time profiles of the working pressure $p_A(t)$ (curve 181), the first cannula flow signal Q(t) (curve 182) and the ventricular pressure $p_{LV}(t)$ in the left ventricle (curve 183) are shown. Here, the suction pressure $p_4$ is set in the filling phase such that the diaphragm fluid pump 2 only fills completely at the beginning of the systole ($t_1$), which can be recognized from the integral (shaded region) of the inlet flow. When filling is detected, the emptying phase is begun by changing to the working pressure p5. This type of synchronization causes high ventricular pressure build-up and reliable heart valve opening.

In a further example, the synchronization is achieved by means of a slower rate variation method compared to the method described above. As already described above, the control unit 4 is adapted to vary a period of the pulsatile fluid flow over a plurality of pumping cycles,

- to detect a change in a maximum value and/or minimum value and/or average value and/or instantaneous value of the first and/or second cannula flow signal, which change is caused by varying the period duration and determined per pumping cycle and
- to determine the time specification such that the maximum value and/or minimum value and/or average value and/or instantaneous value of the first cannula flow signal determined per pumping cycle is maximized or minimized.

Figure 10:
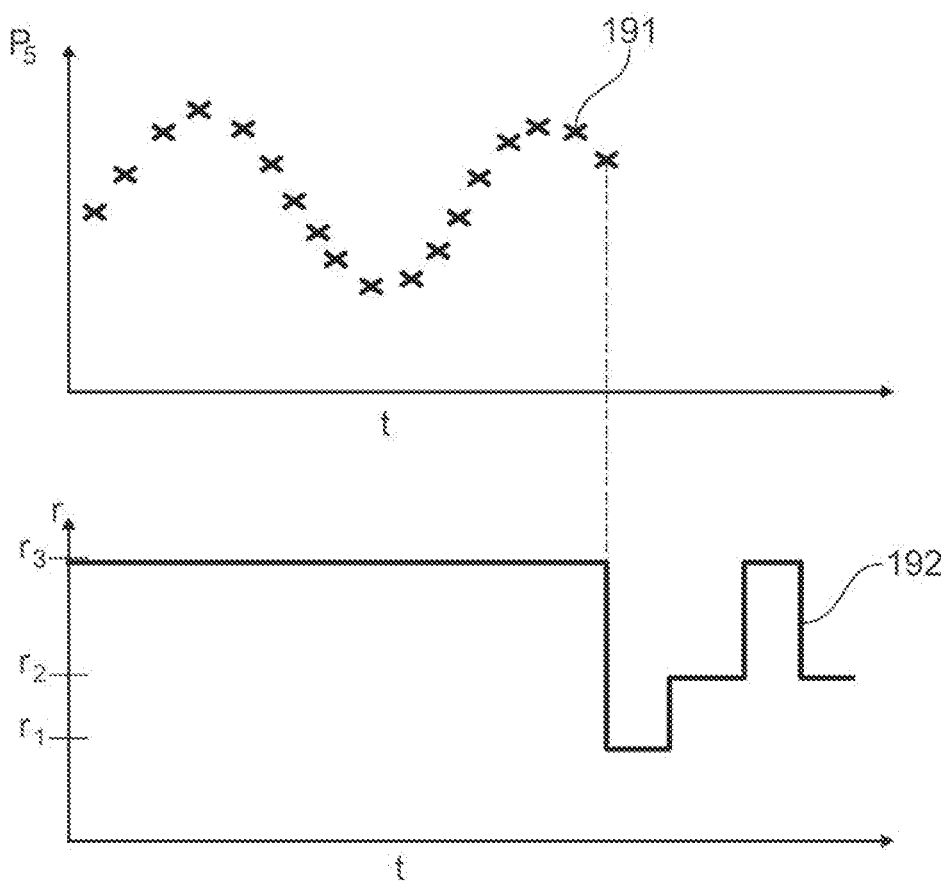
FIG. 10 is a schematic representation of a third example of synchronization.

FIG. 10 shows an example of the rate variation method based on time profiles of the maximum value of the first cannula flow signal (peak flow $p_S$, curve 191) and the pump rate r (curve 192) determined per pumping cycle. The diaphragm fluid pump 2 is initially operated at a rate $r_3$ above the heart rate. The peak flow in the fluid inlet 10 fluctuates periodically. During the decrease in peak flow, a rate $r_1$ is switched to below the heart rate in order to return to the measured maximum of $p_S$. After that, the drive is set to the estimated heart rate. Renewed deviations from the maximum can be corrected by switching to $r_3$ or $r_1$. At the same time, if corrections are necessary, such as the short-term increase to $r_3$ shown, the heart rate estimate can be updated.

In synchronization mode, it is not possible to adjust certain parameters, such as the pump rate, without disturbing the synchronization. However, this can be avoided: the control unit 4 can be adapted to set the average blood flow and/or the relative phase position by omitting one or more half or full pumping cycles (wherein half a pumping cycle can be a filling phase or an emptying phase).

A final example for the control of the diaphragm fluid pump 2 by means of the control unit 4 is particularly suitable for failing Fontan patients, but also has advantages for other patients.

The hemodynamic parameter set here comprises an instantaneous fill level of the diaphragm fluid pump, determined based on an integral of the first cannula flow signal, and the control unit 4 is adapted to compare the instantaneous fill level with an instantaneous setpoint fill level of the diaphragm fluid pump and, if the instantaneous fill level falls below the instantaneous setpoint fill level by at least a predetermined value, to control the working pressure such that the pump rate of the pulsatile fluid flow and/or a suction pressure with which the diaphragm fluid pump is filled is reduced. As already described, the instantaneous setpoint fill level here is a time-variable function that specifies a setpoint fill level of the diaphragm fluid pump 2 at any point in time.

Through this control, the average blood flow adapts to the venous return flow (see Frank-Starling mechanism) and maintains an acceptable physiological pressure in the vena cava (when using pump system 1 as an RVAD) or the pulmonary vein (when using pump system 1 as a LVAD).

In failing Fontan patients, subpulmonary pressures should be maintained between 10 mmHg and 15 mmHg or further reduced during the course of therapy, which, on the one hand, prevents organ problems, and on the other hand, prevents the vena cava from collapsing.

The proposed method for operating the pump system 1 has already been presented in various examples in the description of the pump system 1 and the control unit 4.

The method comprises at least the steps:
- detecting the first cannula flow signal and the working pressure signal,
- determining the time offset and/or the emptying time offset for the first pumping cycle and the first cardiac cycle,
- determining the hemodynamic parameter set based on the time offset and/or the first cannula flow signal and/or the working pressure signal,
- determining the time specification based on the control specification such that the control specification is achieved.

To clarify the use of and to hereby provide notice to the public, the phrases "at least one of <A>, <B>, ... and <N>" or "at least one of <A>, <B>, ... or <N>" or "at least one of <A>, <B>, ... <N>, or combinations thereof" or "<A>, <B>, ... and/or <N>" are defined by the Applicant in the broadest sense, superseding any other implied definitions hereinbefore or hereinafter unless expressly asserted by the Applicant to the contrary, to mean one or more elements selected from the group comprising A, B, ... and N. In other words, the phrases mean any combination of one or more of the elements A, B, ... or N including any one element alone or the one element in combination with one or more of the other elements which may also include, in combination, additional elements not listed. Unless otherwise indicated or the context suggests otherwise, as used herein, "a" or "an" means "at least one" or "one or more."

LIST OF REFERENCE NUMBERS 1 pump system,
2 diaphragm fluid pump,
3 working pressure source,
4 control unit,
5 housing,
6 diaphragm, 7 pump fluid chamber,
8 working fluid chamber,
9 inlet cannula,
10 fluid inlet,
11 outlet cannula,
12 fluid outlet,
13 inlet valve,
14 outlet valve,
15 pressure line,
16 working chamber,
17 electric motor,
18 working piston,
19 control line,
20 working pressure sensor,
21 first flow sensor,
22 second flow sensor,
23 ECG sensors,
24 first cannula pressure sensor,
25 second cannula pressure sensor,
26 display unit,
27 acceleration sensor
91, 92, 93, 101, 102, 103, 111, 112, 113, 121, 122, 131, 132, 141, 142, 143, 151, 152, 153, 161, 162, 163, 171, 172, 172, 181, 182, 183, 191, 192 curves.

The invention claimed is:

1. A pump system comprising
a diaphragm fluid pump which can be fluidically connected to a heart and/or at least one blood vessel by means of an inlet cannula and an outlet cannula and is adapted for generating a pulsatile fluid flow for supporting a cardiac activity of the heart,
a working pressure source connected to the diaphragm fluid pump by means of a pressure line and adapted for providing a working pressure for driving the diaphragm fluid pump,
a control unit adapted for controlling the working pressure,
a first flow sensor adapted for detecting a first cannula flow signal corresponding to an inlet flow in the inlet cannula or an outlet flow in the outlet cannula,
a working pressure sensor adapted for detecting a working pressure signal corresponding to the working pressure in the pressure line,
the pulsatile fluid flow comprising a plurality of consecutive pumping cycles, the cardiac activity comprising a plurality of consecutive cardiac cycles, and each of the pumping cycles comprising a filling phase and an emptying phase,
wherein the control unit is further adapted
  to determine a time offset between a first point in time that occurs during a first pumping cycle and a second point in time that occurs during a first cardiac cycle,
  to determine a hemodynamic parameter set, comprising one or more hemodynamic parameters, based on the time offset and/or the first cannula flow signal and/or the working pressure signal, and
  based on a control specification as a specification for the hemodynamic parameter set and/or for the time offset, to determine a time specification as a specification for a beginning and/or a duration of the filling phase and/or the emptying phase of the first pumping cycle and/or at least one second pumping cycle that occurs temporally after the first pumping cycle such that the control specification is achieved.

2. The pump system of claim 1, wherein the control unit is adapted to control the working pressure based on the time specification such that the control specification is achieved.

3. The pump system of claim 1, further having a display unit, wherein the display unit is configured to display a proposed setting change determined based on the time specification and/or to display at least one hemodynamic parameter of the hemodynamic parameter set.

4. The pump system of claim 1, wherein the hemodynamic parameter set comprises a pump rate of the heart and/or a preload of the heart and/or an end-diastolic pressure and/or an end-diastolic volume and/or an afterload of the heart and/or a contractility of the heart and/or a ventricular pressure and/or a ventricular filling volume and/or an atrial pressure and/or an atrial filling volume and/or a pump filling volume and/or an arterial pressure and/or a venous pressure and/or an average blood flow, determined as an average blood flow through the diaphragm fluid pump averaged over a plurality of pumping cycles, and/or a hydrostatic pressure corresponding to a relative position of the diaphragm fluid pump in relation to the heart.

5. The pump system of claim 1, wherein the control unit is adapted to control the working pressure such that the diaphragm fluid pump is completely filled in the filling phase of each pumping cycle and/or completely emptied in the emptying phase of each pumping cycle.

6. The pump system of claim 1,
wherein the time specification is a specification for the beginning and/or the duration of the filling phase and/or the emptying phase of the first and/or second pumping cycle,
wherein the hemodynamic parameter set comprises an average blood flow, determined as an average blood flow through the diaphragm fluid pump averaged over a plurality of pumping cycles,
wherein the control specification is a specification for the hemodynamic parameter set and
wherein the control unit is further adapted to determine, as a control specification, an increase, decrease or maintenance of the average blood flow based on a time profile of the hemodynamic parameter set.

7. The pump system of claim 6, further having an acceleration sensor, adapted for detecting an acceleration signal corresponding to patient activity, wherein the control unit is adapted to determine the control specification based on the acceleration signal, in particular such that the average blood flow is increased with an increase in patient activity.

8. The pump system of claim 6, wherein the hemodynamic parameter set comprises, in addition to a contractility of the heart, a preload of the heart and/or an afterload of the heart and the control unit is adapted to
  determine a reduction in the average blood flow as a control specification if the time profile of the hemodynamic parameter set comprises an increase in contractility without an increase in preload and/or without an increase in afterload and/or if the time profile of the hemodynamic parameter set comprises a decrease in preload without a decrease in contractility, and/or
  determine that the average blood flow is kept constant as a control specification if the time profile of the hemodynamic parameter set comprises an increase in contractility and an increase in preload and/or afterload, and/or
  determine an increase in average blood flow as a control specification if the time profile of the hemodynamic parameter set comprises an increase in preload without an increase in contractility and/or if the time profile of the hemodynamic parameter set comprises an increase in afterload without a decrease in preload and without an increase in maximum ventricular pressure and/or if the time profile of the hemodynamic parameter set comprises a decrease in contractility without a decrease in preload and/or without a decrease in afterload.

9. The pump system of claim 1, wherein the control unit is adapted to determine the time offset based on the first cannula flow signal.

10. The pump system of claim 9, wherein the control unit is adapted to determine the time offset according to the equation $$T = \frac{\tau}{2\pi} \arg\left(\left[\sqrt{\frac{1}{t_1 - t_0} \int_{t_0}^{t_1} Q(t)^2 \, dt} + i \int_{t_S}^{t_E} \left(\frac{Q(t) - \langle Q \rangle}{\sigma_Q}\right)^3 dt\right] e^{i\alpha}\right).$$

where T is the time offset, τ is a period of the pulsatile fluid flow, Q(t) is a time profile of the first cannula flow signal, t is a time parameter, $t_S$ is the point in time at which Q(t) is less than 20% of $Q_{max}$ for the last time before reaching a maximum flow $Q_{max}$, $t_E$ is the point in time at which Q(t) is less than 20% of $Q_{max}$ for the last time since $Q_{max}$ was reached, <Q> is the average of Q(t) in the time interval from $t_S$ to $t_E$, $\sigma_Q$ is the standard deviation of Q(t) in the time interval from $t_S$ to $t_E$, i is the imaginary unit, α is a predetermined angular offset.

11. The pump system of claim 1, further comprising an ECG sensor adapted for detecting an ECG signal corresponding to an electrical activity of the heart, and/or a first cannula pressure sensor, adapted for detecting a first cannula pressure signal corresponding to an inlet pressure in the inlet cannula or an outlet pressure in the outlet cannula, wherein the control unit is adapted to determine the time offset and/or the hemodynamic parameter set based on the ECG signal and/or the first cannula pressure signal.

12. The pump system of claim 1, wherein the pulsatile fluid flow comprises a measurement phase, wherein the control unit is adapted to set the working pressure to a low working pressure value for the duration of the measurement phase so that a high sensitivity of the first cannula flow signal for pressure changes caused by the first cardiac cycle is achieved.

13. The pump system of claim 2, wherein the time specification is a specification for the beginning and/or the duration of the filling phase and/or the emptying phase of the first and/or second pumping cycle and wherein the control specification is a specification for the time offset such that a specified relative phase position of the pulsatile fluid flow in relation to the cardiac activity is achieved, in particular a co-pulse or a counter-pulse or a pulse delayed by a specified delay interval.

14. The pump system of claim 2, wherein the control unit is adapted to vary a period of the pulsatile fluid flow over a plurality of pumping cycles, to detect a change in a maximum value and/or minimum value and/or average value and/or instantaneous value of the first cannula flow signal, which change is caused by varying the period duration and determined per pumping cycle and to determine the time specification such that the maximum value and/or minimum value and/or average value and/or instantaneous value of the first cannula flow signal determined per pumping cycle is maximized or minimized.

15. The pump system of claim 1, wherein the control specification is a specification for the time offset and wherein the control unit is adapted to change the period of the pulsatile fluid flow over a plurality of pumping cycles in a first direction when a deviation of the time offset determined by the control unit from the control specification is detected, until a sign change of a derivative of a maximum value and/or minimum value and/or mean value and/or instantaneous value and/or another time profile feature of the first cannula flow signal determined per pumping cycle is detected, and is further adapted to change the period of the pulsatile fluid flow in the direction opposite to the first direction when the change of sign is detected.

16. The pump system of claim 1, wherein the control unit is adapted to determine a pressure and/or a pressure change and/or a pressure change rate in a ventricle and/or atrium and/or blood vessel connected to the diaphragm fluid pump based on a time profile of the first cannula flow signal.

17. The pump system of claim 16, wherein the control unit is adapted to vary the time offset by varying the time specification over a plurality of pumping cycles such that the pressure and/or the pressure change and/or the pressure change rate in the ventricle and/or atrium and/or blood vessel connected to the diaphragm fluid pump can be determined based on a change in the time profile of the first cannula flow signal caused by varying the time offset.

18. The pump system of claim 1, wherein the hemodynamic parameter set comprises an instantaneous fill level of the diaphragm fluid pump, determined based on an integral of the first cannula flow signal, and wherein the control unit is adapted to compare the instantaneous fill level with a time-varying instantaneous setpoint fill level of the diaphragm fluid pump and, if the instantaneous fill level falls below the instantaneous setpoint fill level by at least a predetermined value, to control the working pressure such that a pump rate of the pulsatile fluid flow and/or a suction pressure, with which the diaphragm fluid pump is filled, is reduced.

19. The pump system of claim 18, wherein the control unit is further adapted to increase the pump rate of the pulsatile fluid flow over a plurality of pumping cycles until the instantaneous fill level falls below the instantaneous setpoint fill level by at least the specified value, and to then reduce the pump rate of the pulsatile fluid flow.

20. A control unit for a pump system of claim 1, wherein the control unit is adapted for controlling the working pressure and further to to determine the time offset, to determine the hemodynamic parameter set based on the time offset and based on the first cannula flow signal and/or the working pressure signal and to determine the time offset based on the control specification such that the control specification is achieved.

21. A method for operating the pump system of claim 1, comprising:

detecting the first cannula flow signal and the working pressure signal, determining the time offset for the first pumping cycle and the first cardiac cycle, determining the hemodynamic parameter set based on the time offset and based on the first cannula flow signal and/or the working pressure signal, determining the time specification based on the control specification such that the control specification is achieved.

* * * * *